United States Patent [19]

De Mey et al.

[11] 4,446,238
[45] May 1, 1984

[54] BRIGHT FIELD LIGHT MICROSCOPIC METHOD OF LOCALIZING TISSUE ANTIGENS

[75] Inventors: Jan R. De Mey, Turnhout; Marc K. J. J. Moeremans, Mol, both of Belgium

[73] Assignee: Janssen Pharmaceutica N.V., Beerse, Belgium

[21] Appl. No.: 342,552

[22] Filed: Jan. 25, 1982

[30] Foreign Application Priority Data

Mar. 19, 1981 [GB] United Kingdom ............... 8108606

[51] Int. Cl.³ .................... G01N 33/54; G01N 33/74
[52] U.S. Cl. ...................................... 436/527; 424/3; 436/519; 436/801; 436/805; 436/807; 436/817
[58] Field of Search .............. 436/527, 801, 805, 807, 436/817, 519; 424/3

[56] References Cited

U.S. PATENT DOCUMENTS 3,791,932  2/1974  Schuurs ...................... 435/7
4,313,734  2/1982  Leuvering .................. 436/525

OTHER PUBLICATIONS

M. Horisberger et al., The Journal of Histochemistry and Cytochemistry, 25(4), 295-305 (1977).
G. Frens, Nature Physical Science, 241, 29-22, (Jan. 1,1973).
"Immunocytochemistry", 2nd Edition, Ludwig A. Steinberger, Chapt. 5, pp. 104-169, John Wiley & Sons, New York.
J. Gu et al., Regulatory Peptides, 1, 365-374 (1981).

*Primary Examiner*—Sidney Marantz
*Attorney, Agent, or Firm*—Geoffrey G. Dellenbaugh

[57] ABSTRACT

The use of colloidal gold as a bright field light microscopic marker for the immunocytochemical localization of antigens in histological sections, namely the two step or the bridge immuno gold staining method.

2 Claims, No Drawings

BRIGHT FIELD LIGHT MICROSCOPIC METHOD OF LOCALIZING TISSUE ANTIGENS

Since the introduction of the fluorescent antibody technique of Coons, the use of antibodies, as specific probes for the detection of antigens, has expanded enormously. The immunocytochemical approach has broad scientific and diagnostic importance. Current immunocytochemical techniques for localizing antigens in histological sections (plastic, paraffin or cryostat sections) at the light microscopic level are based on the labeling of specific ligands with fluorescent dyes or various enzymes. Besides antibiotics, other reagents such as protein A, the avidin/biotin system, or labeled antigens have been used for the indirect detection of immunoreactive antigens. The development of the hybridoma technique for the production of monoclonal antibodies is another very important new development.

For light microscopy the indirect immunofluorescence method and the unlabeled antibody-enzyme method, e.g., the peroxidase-antiperoxidase (PAP) method, are by far the most widely used. See, for example, Immunocytochemistry (second edition), Ludwig A. Steinberger, John Wiley & Sons, New York—Chichester—Brisbane—Toronto. The PAP-method has become especially popular. The principals of this bridge method allow for high sensitivity and low background, with the advantage of producing permanent preparations which can be objected with classical objects.

There is however a need for alternative methods since the peroxidase technique uses toxic products for the enzymatic reaction, and endogenous peroxidase activity sometimes obscures the antigen staining. In addition, at present, there is no commercially available mouse or rat PAP complex for use with the increasing number of mouse or rat monoclonal antibodies.

The present invention is concerned with a novel bright field light microscopic immunocytochemical method for the localization of antigens in histological sections, said method using colloidal gold labeled immunoglobulins as a red coloured marker, this marker being able to function as antibody in a two step procedure or as antigen in a three step, bridge method.

In analogy with the Immuno Fluorescence Staining method, the method of the present invention will be named hereinafter as the Immuno Gold Staining (IGS) method.

In the two step method a suitable primary antibody reacts with the tissue antigens and, subsequently, the specific binding sites where the primary antibody is attached are detected with colloidal gold granules coated with the secondary anti-antibodies.

In the three step bridge method a suitable primary antibody reacts with the tissue antigens, subsequently, secondary unlabeled anti-antibodies are applied in such an excess that they react with the primary antibodies with only one of their two combining sites and, finally, the free sites of the anti-antibodies react with colloidal gold granules coated with γ-globulins prepared from pre-immune serum of the same animal species as the primary antibodies.

In both procedures the end-product is an accumulation of large numbers of gold granules over antigen-containing areas, thus yielding the typical reddish colour of colloidal gold sols.

The IGS-methods can be applied to all antigens contained in sections of paraffin or plastic unbedded tissues, as well as cryostat sections. Unlike immuno-enzyme procedures, the IGS-methods do not need any subsequent reaction to develop a visible stain. The development of the colour can be monitored under the microscope, since no visible backgroun staining is developing during the incubation step.

The bridge IGS-method in particular gives very satisfactory results and yields as colourful and contrasting a picture as the PAP-procedure.

The IGS-reagents have the additional advantage in that they are very easy to produce, and remain stable for long periods. For the bridge IGS-method, IGS-reagents useful for any kind of primary antibody can be obtained, by simply preparing the gold labeled γ-globulin of the same animal species as the primary antibody. This advantage can make the IGS-method very useful in combination with the very high specificity, achieved by mouse or rat monoclonal antibodies.

The bridge IGS-method has all the advantages of other bridge methods. An additional advantage is the fact that IGS-reagents can be produced on a large scale at low cost. The immunoglobulins can be prepared from pre-immune serum. Unlike enzyme-antibody conjugates, which lose their antigenic properties but retain antibody activity, the IGS-reagents retain both antigenic and antibody properties. It is this interesting property, together with the remarkably well visable red colour that provides the basis of the present invention.

Preparation of colloidal gold-labeled γ-globulins

The colloidal gold sol with gold granules of 18–20 nm mean diameter are prepared according to Frens.

γ-Globulins from pre-immune rabbit and rat serum are prepared by affinity-chromatography on Protein-A-Sepharose-4B. Goat antibodies against rabbit immunoglobulin G are purified from immune serum by affinity chromatography on rabbit γ-globulins G-Sepharose-4B.

The purified γ-globulins or antibodies are dialyzed against 2 mM borax buffer, pH 9.0. This prevents precipitation and denaturation of the antibodies at low pH or ionic strength. The gold sol is adjusted to pH 9.0 with potassium carbonate just before use. The protein solution is centrifuged at 100.000 g for 1 hour at 4° C. to remove aggregates.

The optimal amount of protein, necessary to mobilize the gold sol against flocculation in 1% NaCl is determined from a concentration variable isotherm. The optimal amount of protein +20% ($\pm 1$ ml (1 mg/ml) for 100 ml of gold sol), was added dropwise but quickly to the gold sol at room temperature. After 1-2 minutes gently stirring a 10% Bovine Serum Albumin (BSA) stock solution in 2 mM borax buffer, pH 9.0, is added to a final concentration of 1%. Unbound proteins are removed by three cycles of centrifugation (12.000 g, 4° C., 1 hour) and resuspended in 1% BSA/TBS pH $8.2 + 2.10^{-2}$ M sodium azide. This buffer is found optimal for preventing subsequent aggregation of the colloidal gold labeled immunoglobulings.

The last pellet is resuspended in 1% BSA buffer to give an $OD_{520\ nm} = 0.5$ to 1 when diluted 1/20 in this buffer. This preparation is called GARG 20 when secondary antibodies to, for example, rabbit immunoglobulin are used or RIGG 20 when normal rabbit immunoglobulin G is coupled to gold of 20 nm diameter. Larger particles, e.g. 40 nm diameter, can also be used and sometimes give darker staining.

In the present invention all known methods for tissue preparation, used for antigen localization, may be used. Very important is the use of high quality primary antisera or purified antibodies.

The following examples are intended to illustrate and not to limit the scope of the present invention.

EXAMPLES

Example I

Demonstration of somatostatin-containing cells in guinea pig antrum with the two step IGS-method using rabbit anti somatostatin-thyroglobulin complex antiserum Tissue samples are fixed in Bouin-Hollande sublimé and embedded in paraffin following art-known methods. 5 μm sections are deparaffinized and sublimate crystals dissolved with lugol and sodium hyposulfite. After washing, the preparations are ready for immunostaining. They are first incubated with 5% normal goat serum (NGS) in 10 mM Tris buffered saline (TBS) pH 7.6 for 30 min. and then with antiserum, appropriately diluted in 1% NGS/TBS, overnight at room temperature. The sections are washed with 0.1% BSA buffer pH 8.2 (3×10 min) and further incubated with GARG 20 diluted 1:5 with 1% BSA buffer for 2 hours. The development of the stain can be followed with bright field light microscopy. The preparations are then washed with 0.1% BSA buffer (3×10 min) and mounted in DPX or similar mounting medium. Counterstaining with aqueous methyl green is sometimes advantageous.

Example II

Demonstration of 5-HT (serotonin) containing cells in guinea-pig duodenum with the bridge IGS-method using rabbit anti 5-HT thyroglobulin complex antiserum A small piece of tissue is frozen in Arcton and freeze-dried overnight at −40° C. It is then fixed in benzoquinone vapour (60° C., 3 hours) and embedded in paraffin wax. Sections (10μ) are cut and mounted in uncoated slides.

Deparaffinized sections are first incubated with 5% normal goat serum (NGS) in TBS for 30 min. and then with antiserum appropriately diluted in 1% NGS/TBS, overnight at room temperature. The sections are washed with TBS, 3×10 min. and further incubated with GAR/IgG antiserum diluted 1:20 in TBS for 1 hour at room temperature. They are washed with 0.1% BSA buffer pH 8.2 (3×10 min.) and then incubated with RIG G20 1:5 for 2 hours. The development of the stain can be followed with bright field light microscopy. The preparations are then washed with 0.1% BSA buffer 3×10 min. and mounted as in Example I.

What is claimed is:

1. A two step indirect bright field light microscopic method for the detection of antigens in tissue sections, which method comprises the steps of
    (i) preparing the tissue sections;
    (ii) reacting the tissue sections with primary antibodies specific to said antigens;
    (iii) detecting the specific binding sites, where the primary antibodies are attached, with colloidal gold granules coated with secondary antibodies specific to said primary antibodies; and
    (iv) mounting the sections.

2. A three step bridge bright field light microscopic method for the detection of antigens in tissue sections, which methods comprises the steps of
    (i) preparing the tissue sections;
    (ii) reacting the tissue sections with primary antibodies specific to said antigens;
    (iii) applying secondary unlabeled anti-antibodies in such an excess that they react with the primary antibodies with only one of their two combining sites;
    (iv) reacting the free sites of the said anti-antibodies with colloidal gold granules coated with γ-globulins, prepared from pre-immune serum of the same animal species as the primary antibodies; and
    (v) mounting the sections.

* * * * *